(12) United States Patent
Park (10) Patent No.: US 6,432,800 B2
(45) Date of Patent: Aug. 13, 2002

(54) INSPECTION OF DEFECTS ON THE CIRCUMFERENCE OF SEMICONDUCTOR WAFERS

(75) Inventor: Keun-Hyung Park, Chongju-Shi (KR)

(73) Assignee: Selight Co., Ltd., Kyonggi-do (KR)

( * ) Notice: Subject to any disclaimer, the term of this patent is extended or adjusted under 35 U.S.C. 154(b) by 0 days.

(21) Appl. No.: 09/776,382

(22) Filed: Feb. 2, 2001

(30) Foreign Application Priority Data

Feb. 3, 2000 (KR) .............................................. 00-5400

(51) Int. Cl.[7] .............................................. H01L 21/44
(52) U.S. Cl. ...................................................... 438/582
(58) Field of Search .................. 438/14, 582; 364/148, 364/552

(56) References Cited

U.S. PATENT DOCUMENTS

| | | |
|---|---|---|
| 4,118,730 A | 10/1978 | Lemelson |
| 4,148,061 A | 4/1979 | Lemelson |
| 4,338,626 A | 7/1982 | Lemelson |
| 4,511,918 A | 4/1985 | Lemelson |
| 4,979,029 A | 12/1990 | Lemelson |
| 4,984,073 A | 1/1991 | Lemelson |
| 5,067,012 A | 11/1991 | Lemelson |
| 5,119,190 A | 6/1992 | Lemelson |
| 5,351,078 A | 9/1994 | Lemelson |
| 5,619,429 A * | 4/1997 | Aloni .......................... 364/552 |

* cited by examiner

Primary Examiner—John F. Niebling
Assistant Examiner—Andre C Stevenson
(74) Attorney, Agent, or Firm—Knobbe, Martens, Olson, & Bear, LLP.

(57) ABSTRACT

The inspection apparatus inspects defects of wafer circumference by processing the image information of the wafer circumference. The inspection apparatus includes a wafer moving unit and an image information acquisition unit. The moving unit accommodates the semiconductor wafers and either moves the wafers linearly or rotates the wafers. The moving unit moves the wafers linearly in a direction of the plane of the wafers when the image information of a linear portion of the wafer is being obtained by the image information acquisition unit. The moving unit rotates the wafers when the image information on a round portion of the wafer circumference is being obtained.

36 Claims, 7 Drawing Sheets

INSPECTION OF DEFECTS ON THE CIRCUMFERENCE OF SEMICONDUCTOR WAFERS

BACKGROUND OF THE INVENTION

1. Field of the Invention

This invention relates to inspecting flaws in semiconductor wafers. More particularly, this invention relates to inspecting defects on the circumference of semiconductor wafers.

2. Description of the Related Technology

Semiconductor wafers used in integrated circuit fabrication processes are generally thin circular semiconductor plates. The semiconductor wafers undergo thermal and physical stresses during various treatments of the fabrication processes. Sometimes, wafers have some internal or surface defects such as cracks and scratches. The portions of the wafers having such defects may produce defective integrated circuits, reducing the yield of the fabrication processes. Also, an existing crack or other defects of a wafer may aggravate by thermal and physical stresses applied thereto during the fabrication processes.

Wafers having such defects may cause more serious problems. For example, if a defective wafer breaks during the processes, the wafer can no longer be used. Also, if multiple wafers are processed simultaneously in the same chamber as is common in an automated fabrication process, pieces of a broken wafer may scratch or harm many other flawless wafers in the same batch. The broken pieces may damage the expensive semiconductor fabrication equipment.

SUMMARY OF THE INVENTION

One aspect of the present invention provides an apparatus for inspecting defects of a semiconductor wafer. The wafer is a thin plate comprising two surfaces and a circumference neighboring the two surfaces. The apparatus comprises a wafer holder; a camera configured to capture images of a circumference of a wafer subject to the inspection and to generate data of the captured images; and a processor configured to process the data from the camera so as to identify defects on the circumference of the wafer.

In the apparatus, the camera is configured to continuously capture the images of the circumference. The apparatus further comprises a mechanism configured to effect at least one of linear movement of a camera location and changes of a camera direction. The apparatus further comprises a light source configured to illuminate the circumference of the wafer. The light source comprises a longitudinal light bulb having a longitudinal direction, and the wafer holder is configured to hold the wafer such that the two surfaces of the wafer is substantially parallel to the longitudinal direction of the light bulb. The wafer holder is configured to hold the wafer in a way that the camera captures the images of the circumference of the wafer. Also, the wafer holder is configured to hold a plurality of wafers, which are concurrently subject to the inspection.

The apparatus further comprises a mechanism configured to couple with the holder, wherein the mechanism is configured to move the wafer held in the holder without changing a distance between the camera and a point on the circumference of the wafer, which is the closest from the camera. The apparatus mechanism comprises a lower support table and an upper linear motion table configured to linearly move on the lower support table while being coupled therewith. The upper linear motion table is configured to couple with the wafer holder. The mechanism further comprises an actuator driving the upper linear motion table to linearly move. The mechanism is configured to rotate the wafer held in the holder about an axis substantially perpendicular to the surfaces of the wafer. The wafer holder comprises a flat aligner, which further comprises the mechanism configured to rotate the wafer. The apparatus further comprises a mechanism configured to keep an angle between a central axis of a lens of the camera directing a point on the circumference and a tangent of the point constant during the capturing images. The apparatus further comprises a display configured to display inspection results; an input device configured to input information relating to the wafer subject to the inspection and commands to the apparatus; a memory configured to store image data of circumference of the wafer. The camera comprising a charge coupled device (CCD) line scan camera.

Another aspect of the present invention provides a method of inspecting defects on a circumference of a semiconductor wafer. The method comprises: obtaining images of a circumference of a semiconductor wafer; generating data indicative of the images of the circumference; and processing the data, thereby identifying defects on the circumference of the semiconductor wafer.

In the method, the step of obtaining images comprises capturing images of an entire circumference of the wafer with a camera. Also the step comprises moving at least one of the wafer and the camera. The moving is performed without changing a distance between the camera and a point on the circumference of the wafer, which is the closest from the camera. In case the wafer circumference comprises a round portion and a linear portion, the linear moving is performed during capturing images of the linear portion, and the rotation is performed during capturing images of the round portion.

Also, the moving comprises rotating the wafer about an axis substantially perpendicular to the surfaces of the wafer. The wafer surfaces are substantially circular and the axis is a central axis of the circular surfaces. In capturing images while rotating the wafer, the camera directs the central axis of the circular surfaces. The obtaining images comprise capturing images of circumference of a plurality of wafers. Also, during the capturing images, an angle between a central axis of a lens of the camera directing a point on the circumference and a tangent of the point is kept constant. The method further comprises illuminating the circumference of the wafer during the obtaining of the images. The illuminating comprises illuminating the circumference with a longitudinal light source having a longitudinal direction, in which the longitudinal direction of the light source is substantially parallel to the surfaces of the wafer.

Further, the present invention provides a method of fabricating integrated circuits on a semiconductor wafer. This method comprises inspecting defects on a circumference of a semiconductor wafer, and thereafter subjecting the semiconductor wafer to at least one of chemical and thermal treatments, thereby fabricating integrated circuits. The inspection comprises: capturing images of a circumference of a semiconductor wafer; generating data indicative of the images of the circumference; and processing the data, thereby identifying defects on the circumference of the semiconductor wafer. The inspection stage may also have all the features of the method of inspecting defects as summarized above.

DETAILED DESCRIPTION OF THE PREFERRED EMBODIMENT

Figure 1:
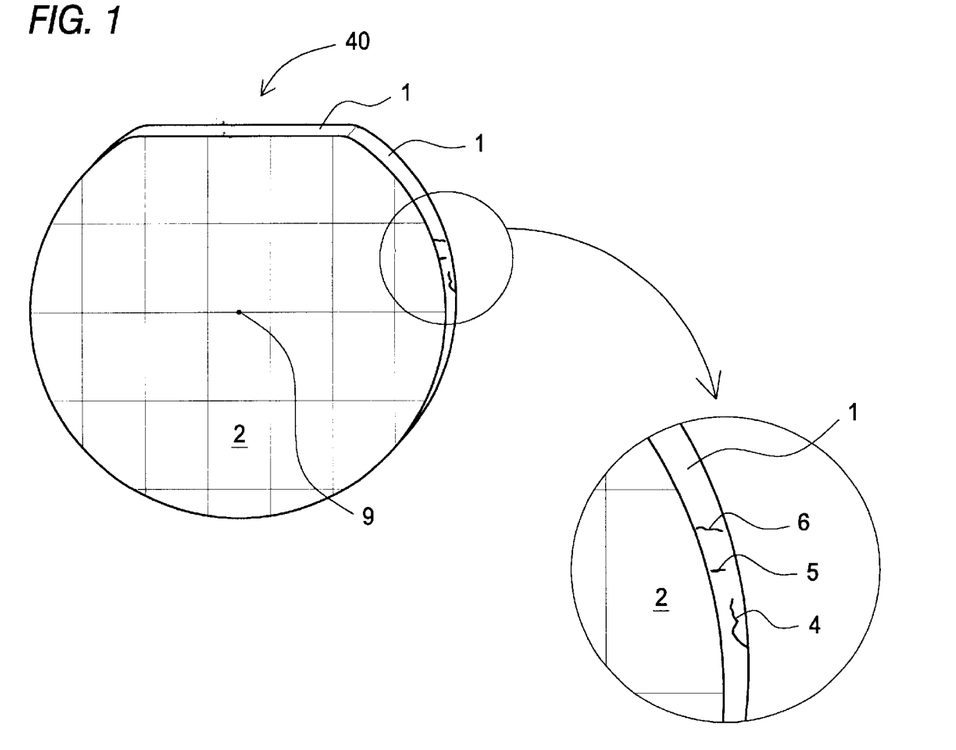
FIG. 1 shows a semiconductor wafer with an enlarged view of a portion of its circumference.

Defects in the semiconductor wafers may exist on the surface 2 or in the interior of its thin body, as discussed in the Description of Related Technology, supra. As shown in FIG. 1, defects of wafers may also exist on the circumferential area 1 of the wafer, which forms a thickness of the thin wafer body. This area is referred to as "circumference" 1 for the sake of convenience. The enlarged portion of FIG. 1 illustrates examples of cracks and scratches 4, 5 and 6 (collectively "defects" or "flaws") on the circumference 1. These defects may further aggravate by the thermal and physical stresses applied to the wafer 40 during the semiconductor fabrication processes. This aggravation may cause serious losses. As mentioned in the Summary of the Invention, supra, various aspects of the present invention provide method and apparatus, inspecting wafers to detect defects or flaws on the circumference. These aspects and other features of the present invention will now be discussed in detail in terms of certain embodiments.

Figure 2:
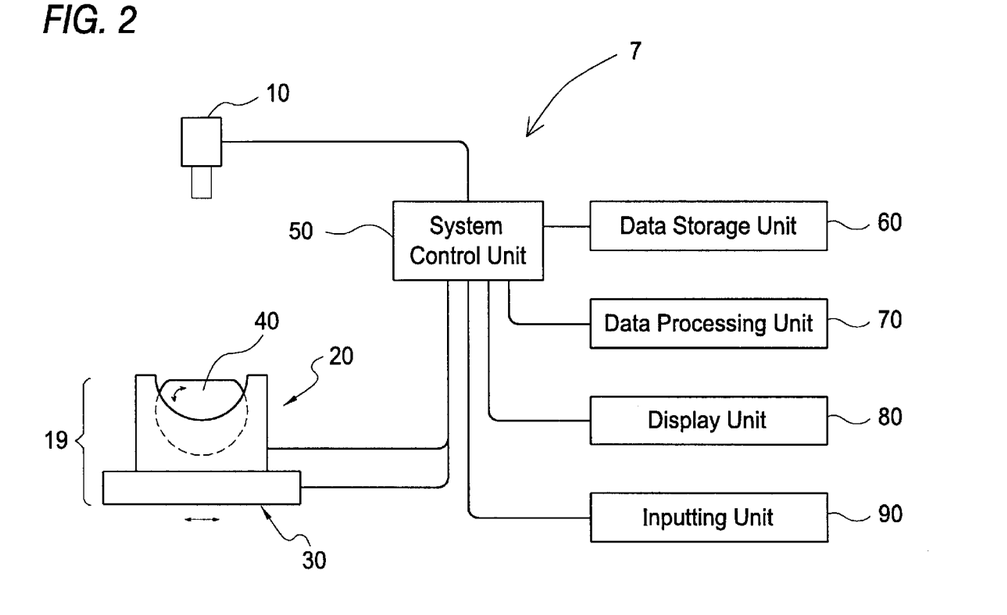
FIG. 2 is a conceptual construction of a system inspecting defects on the circumference of semiconductor wafers according to the present invention

FIG. 2 conceptually illustrate a system 7, inspecting semiconductor wafer 40 to detect defects or flaws 4, 5, and 6 on the circumference 1 in accordance with one embodiment of the present invention. The system includes an image information acquisition unit 10, a wafer moving unit 19, a data storage unit 60, a data processing unit 70, a display unit 80, an input unit 90, and a system control unit 50. The wafer-moving unit 19 includes a linear moving mechanism 30 and a wafer holder or container called flat aligner 20.

In the system 7, the image information acquisition unit 10 captures the images of the circumference 1 of wafer 40 as the wafer-moving unit 19 moves the wafers 40. The images captured are temporarily stored in the data storage unit 60, or alternatively without such temporal storage, and processed by the data processing unit 70 to detect flaws on the circumference 1 of wafer 40. If necessary, some data, e.g., for identifying wafers, may be entered using the inputting unit 90. The processed test data can be displayed on the display unit 80. All of the sub-units of the system 7 are connected to the system control unit 50, which controls the overall operation of the system 7 including image acquisition, data processing and displaying.

Figure 3:
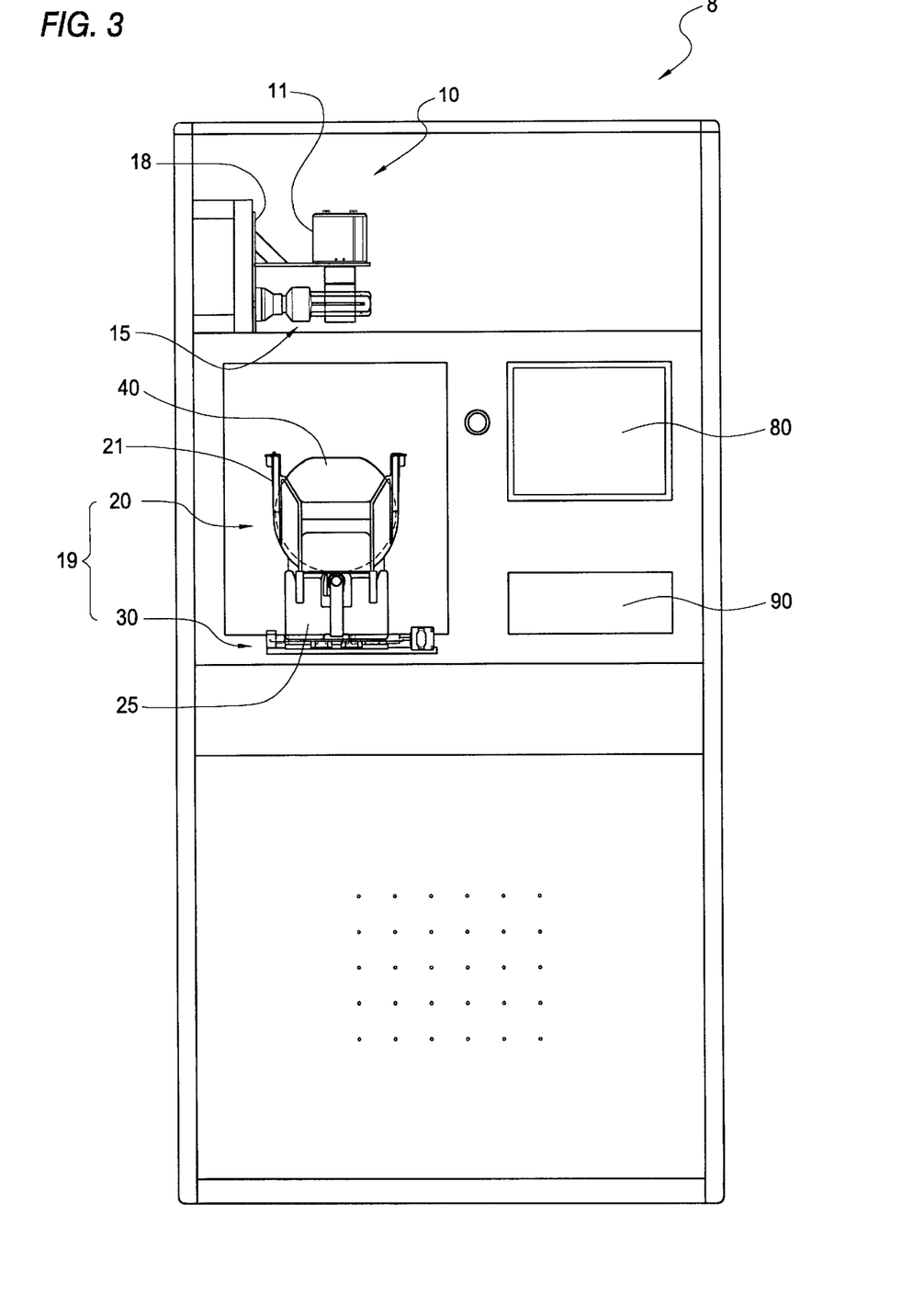
FIG. 3 is a front view of a wafer inspecting apparatus implementing the system of FIG. 2.
Figure 4:
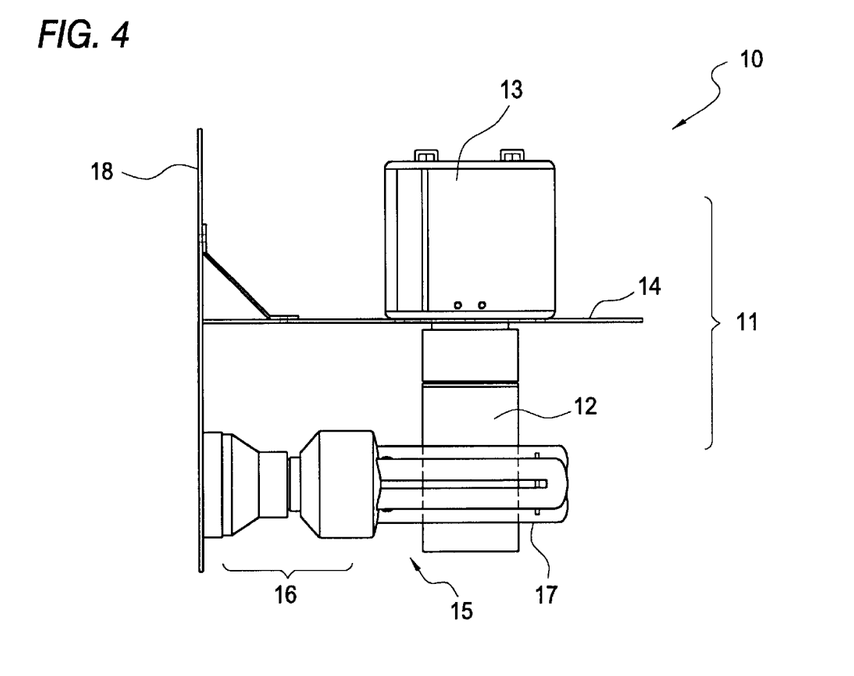
FIG. 4 is a front view of the image information acquisition unit of the wafer inspecting apparatus of FIG. 3.
Figure 5:
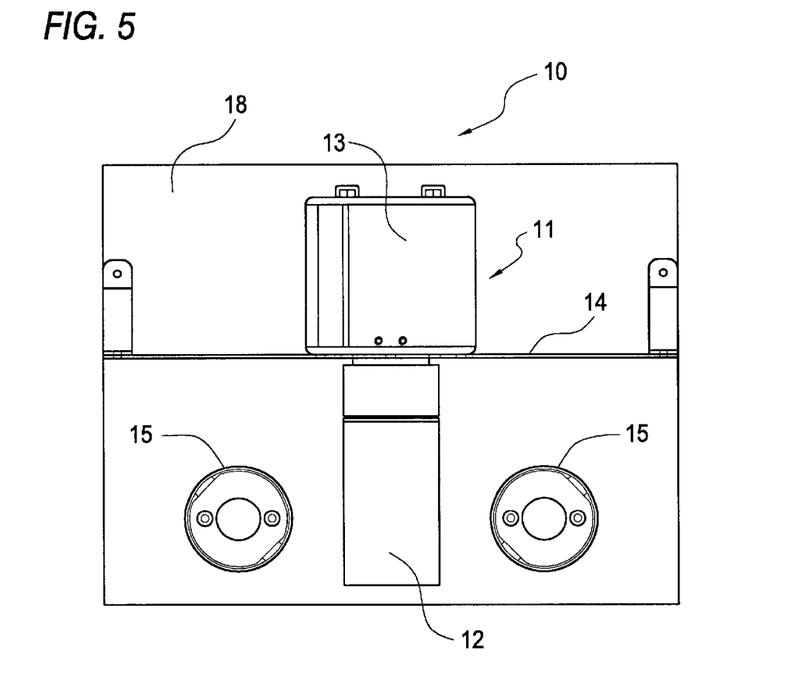
FIG. 5 is a side view of the image information acquisition unit of the wafer inspecting apparatus of FIG. 3.

FIG. 3 illustrates a wafer circumference inspection apparatus 8 implementing the system 7 of FIG. 2. FIGS. 4–7 further illustrate portions of apparatus 8. Referring to FIGS. 3, 4 and 5. Advantageously, the image information acquisition unit 10 includes a camera 11 and a light source 15. For example, the camera 11 and the light source 15 are installed respectively on a horizontal support 14 and a vertical support 18, both of which are fixed to a main body of the inspecting apparatus 8. The camera has a lens 12 and a body 13. The body 13 is fixed on the horizontal support 14 such that the lens faces down at the wafers placed below.

Preferably, the camera 11 is a digital line scan camera. Because the length of defects on the circumference 1 is normally less than 0.5 mm, high resolution image capturing is required. Particularly, a charge coupled device (CCD) line scan camera with greater than 2,084 pixels allows such high-resolution image scanning for an effective inspection of wafer circumference 1, although not limited thereto. For example, DALSA CL-CB 2048 line scan camera available from DALSA Inc. www.dalsa.com) can be used.

The light source 15 includes lamps 17 and sockets 16. Advantageously, two lamps 17 one on each side of the lens 12 of a camera 11 are used. A three phase fluorescent bulb is advantageously used as the lamp 17. As shown in FIG. 3, the light bulb is preferably arranged such that its longitudinal direction is parallel to the circumference of the wafer. Also, the light source 15 preferably is arranged such that the light from the light source does not directly shine the lens 12 of the camera 11. The intensity of the light from the light source 15 can be adjusted depending upon various parameters, including the camera sensitivity, the distance between the lamp 17 and the wafer 40, the distance between the wafer 40 and the camera lens 12, etc. The socket 16 of the light source 15 is fixed on and supported by the vertical support 18. This vertical support 18 is fixed in the inspection apparatus 8.

Figure 6:
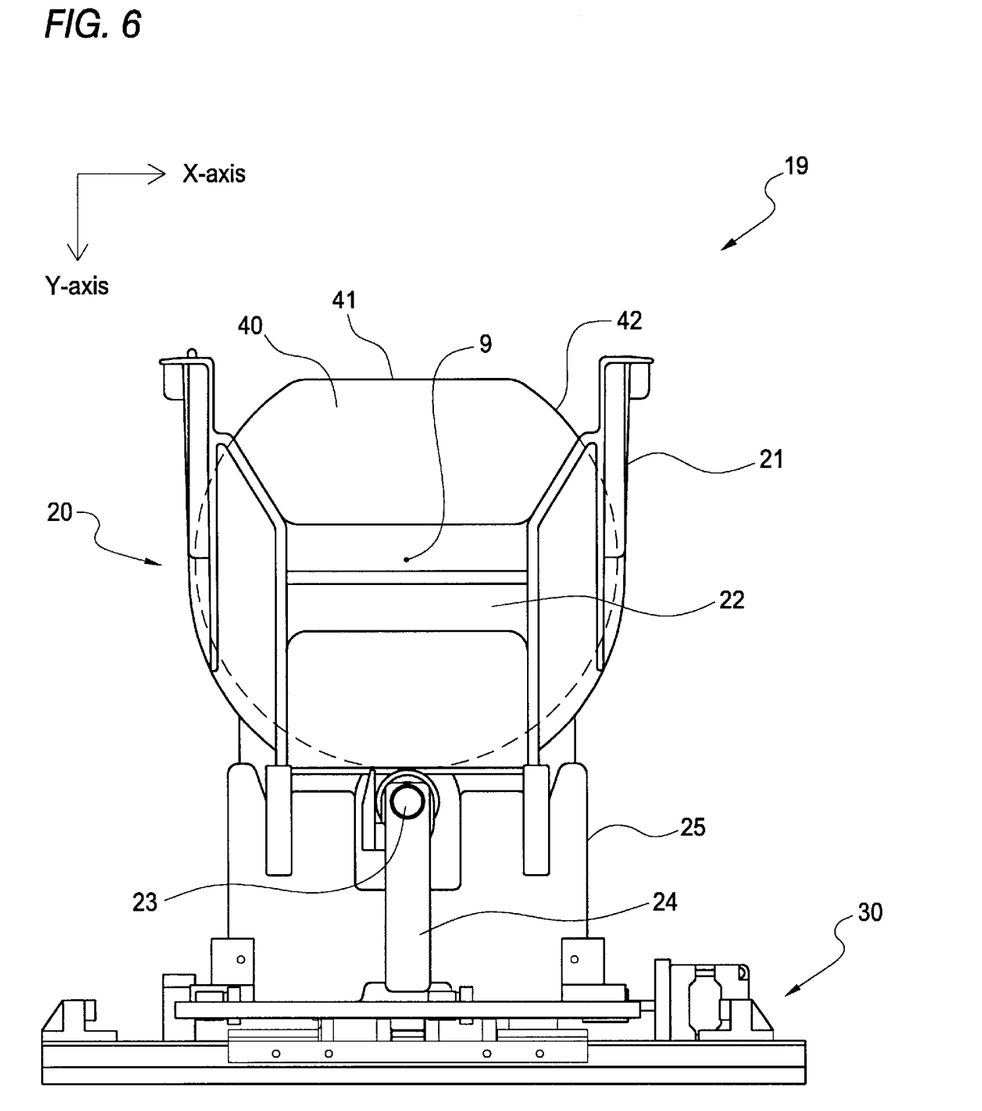
FIG. 6 illustrates a wafer-moving unit of the wafer inspection apparatus of FIG. 3.

Referring to FIGS. 2, 3 and 6, the wafer-moving unit 19 is now further discussed. The flat aligner 20 contains wafers and enables rotation of the wafers about an axis perpendicular to their surface 2. Although only one wafer 40 is shown, the flat aligner 20 may contain a number of wafers aligned in parallel. The linear moving mechanism 30 is configured to linearly move the flat aligner 20; i.e., the wafer 40 contained in the flat aligner 20 linearly moves relative to the camera 11. For example, the flat aligner 20 is moved in the directions illustrated by the two-sided arrow below the mechanism 30. In the alternative, the camera 11 with the light source 15 can be configured to linearly move to effect the relative movement of the wafer 40.

The flat aligner 20 includes a cassette 21 and a frame 25 located below the cassette 21. The cassette 21 is designed to hold a plurality of wafers 40 in parallel, for instance, 25 or 50 wafers. The cassette 21 includes side supports 22 at both sides, which form wafer slots to keep a space between the neighboring wafers 40. The frame 25 is equipped with a vertical support 24 to support a roller 23 at its top. The roller 23 supported by the vertical support is mounted at the bottom of the cassette 21 such that the circumferential surface (not shown) of the roller 23 can contact the circumference 1 of each of the plurality of the wafers 40. When the roller 23 rotates in contact with the round portion of circumference 1 of the wafer, the wafer 40 also rotates about its central axis 9 (FIGS. 1 and 6) perpendicular to its surface 2. A flat aligner 20 can be instantly assembled by mounting a cassette 21 on top of a frame 25. Alternatively, a flat aligner 20 is integrally formed with portions corresponding to the cassette 21 and the frame 25. For example, EZ Guide Flat Finder available from H-Square Company can be used as the flat aligner 20.

Figure 7:
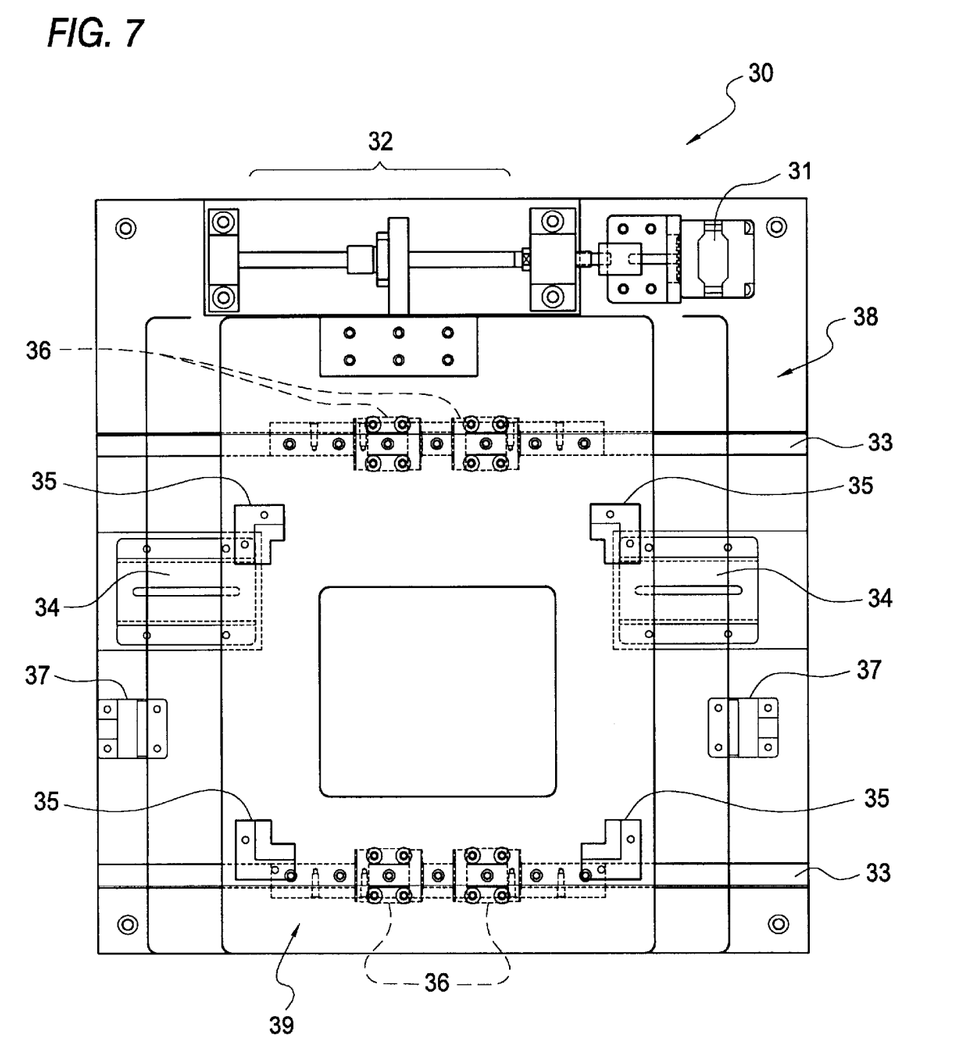
FIG. 7 is a horizontal view of the linear moving mechanism of the wafer-moving unit of FIG. 6.

Referring to FIGS. 6 and 7, the linear moving mechanism 30 includes upper and lower tables 38 and 39, guidance units, and a driving unit. The upper and lower tables 38 and 39 are shaped wide and rectangular, with the upper linear motion slide table 39 positioned on the lower support table 38. On the upper table 39, flat aligner holders 35 which supports and secures the flat aligner 20 are installed. Four flat aligner holders 35 on the upper table 39 form a rectangular shape, although not limited thereto. Two stoppers 37 that limit the range of movement of the upper table 39 are installed on both sides of the lower table 38.

Each guidance unit includes guide rails 33 and linear bearings 36, and guides relative motions of upper and lower tables 39, 38. Advantageously, two guide rails 33 are fixed in parallel on the top surface of the lower table 38. Advantageously, the guide rails 33 extend in the direction parallel to the surface 2 of the wafer 40 when contained in the flat aligner 20. The linear bearings 36 are fixed to the lower surface of the upper table 39 so that they can engage and cooperate with the guide rail 33. The guide rails 33 and linear bearings 36 enable the upper table 39 to linearly move relative to the lower table 38 in the direction parallel to the surface 2 of the wafer 40.

The driving unit includes a step motor 31, a ball screw 32, and sensors 34, all of which are preferably installed in the lower table 38, and drives the linear motions of the upper table 39. The step motor 31 is activated by the operating signals sent from the system control section 50, and it provides the driving force for moving the upper table 39 linearly above the lower table 38. The ball screw 32 connected to the upper table 39 transforms the rotation of the step motor 31 into the linear motion and transmits this linear motion to the upper table 39. The sensors 34 are configured to detect the position of the upper table 39, and transmit the positional signals to the system control unit 50, so that the control unit 50 can control the stop, changes of directions and linear motions of the upper table 39.

The system control unit 50 directly or indirectly connected to all the sub-units of the apparatus and controls the operations of them. As the system control unit 50, any programmable microprocessor can be used. The system control unit 50 may also be incorporated in the control unit of the overall semiconductor fabrication processes.

The data storage unit 60 connected to the system control unit 50 and is configured to store data including the image information of the wafer circumference 1 acquired by the camera 11. It also stores the data processed by the data processing unit 70 discussed below. A hard disk drive or any other data storage device can be used for this data storage unit 60.

The data processing unit 70 is also connected to the system control unit 50 and is configured to process image information of the wafer circumference 1 stored in the storage unit 60 or received directly from the image information acquisition unit 10. The processing the image information is to detect defects or flaws on the wafer circumference 1. Any data processing techniques can be used to detect defects or flaws from the information indicative of captured images of wafer circumference 1. The processed results are then transmitted to the display unit 80 and/or to the data storage unit 60 for storage. Any suitable microprocessor can be used as the data processor unit 70. The data processing unit 70 may be incorporated in a microprocessor constituting the system control unit 50.

The display unit 80 is connected to the system control unit 50. Alternatively, it may be directly connected to the data processor unit. The results of the data processing by the data processing unit 7 are displayed on the display unit 80. As the display unit 80, a conventional video monitor can be used. A touch screen may be used as the display unit 80 in conjunction with the input unit 90, which will be described below.

The input unit 90 connected to the control unit 50 is to input commands to the apparatus 8 for storing image data, processing, activating the wafer moving unit 19, activating the image information acquisition unit 10, etc. As the input unit 90, a keyboard, a touch screen, or a mouse can be used.

In this embodiment, the wafer moving unit 19 is described to include the flat aligner 20 and the linear moving mechanism 30, but this invention is not limited to the above configuration. If a device can make the wafer 40 undergo rotation and/or linear motion, it can be used as the wafer-moving unit 19. Other parts may also be modified to meet the purpose of this invention. It can readily be seen to those skilled in the art that these modifications are within the scope of this invention.

Figure 8:
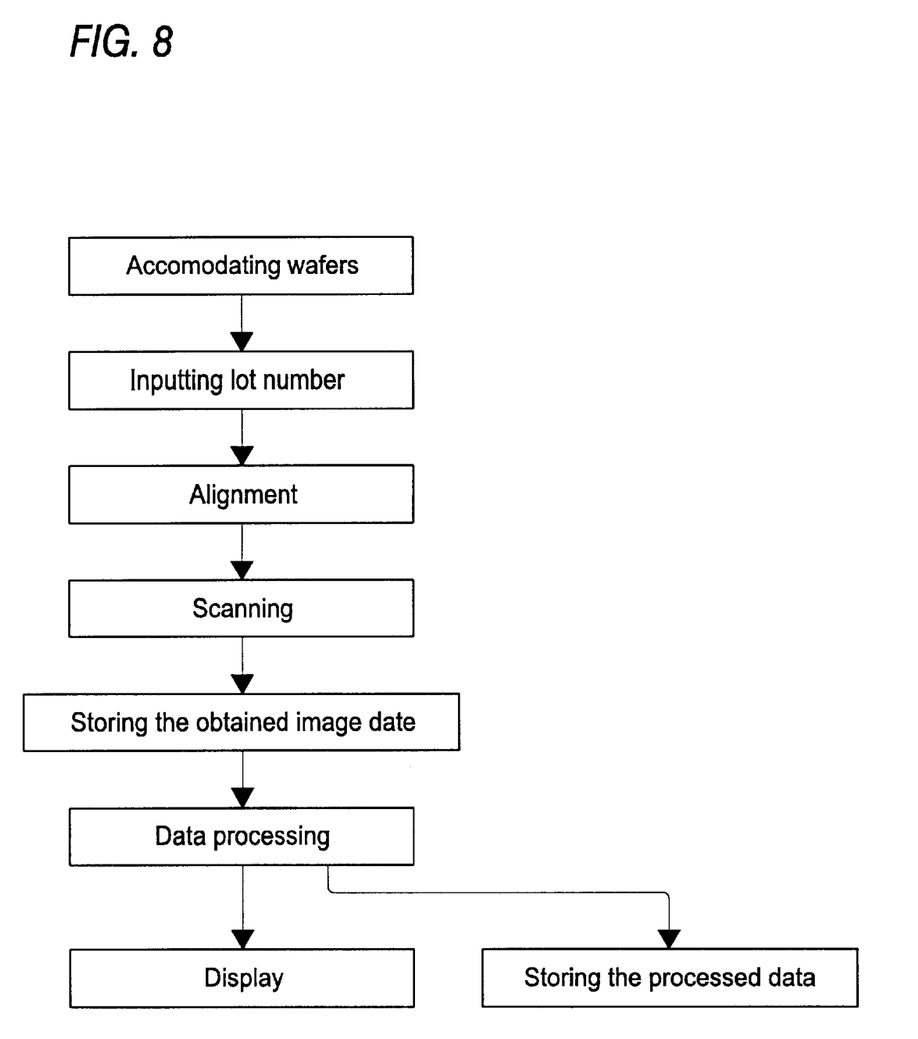
FIG. 8 is a flowchart of the process for inspecting defects on the wafer circumference in accordance with an embodiment of the present invention.

FIG. 8 is an exemplary flow chart of the wafer circumference inspection process, which can be used in connection with the inspection apparatus 8. First, a plurality of wafers 40 are loaded in the slots of the cassette 21 of the flat aligner 20. The wafers are placed in the cassette 21 such that the surfaces 2 of the wafers 40 are parallel to one another. The flat aligner 20 containing the wafers 40 is mounted on the linear moving mechanism 30 in a way that the moving direction of the linear moving mechanism 30 is parallel to the surface 2 of the wafers.

After the flat aligner 20 containing wafers 40 is mounted on the linear moving mechanism 30, the lot numbers of the wafers 40 are inputted by using the inputting unit 90. A lot number generally consists of combination of the wafer type, manufacturer, inspection date, serial number, and the like.

Once the lot numbers are entered, the position of the wafers 40 within the slots of the cassette 21 is arranged. First, a reference or starting point on the circumference 1 of a wafer is determined so that the relative position of any defects with respect to the reference point can be traced down after the wafer 40 has undergone rotations and linear motions. One of the two junctions of the linear portion 41 and the circular portion 42 of the circumference of the wafer 40 can be used as the reference point. Supposed that the X-Y plane of Cartesian coordinate is on the wafer surface as shown in FIG. 6, the wafers 40 are arranged so that the pre-determined reference point of each wafer has the same X and Y coordinate values. In other words, pre-determined reference points of all of the wafers in the cassette 21 are aligned in a straight line perpendicular to the surface of the wafers.

Once the wafers 40 are properly arranged, the camera 11 starts to scan and capture images of the circumference 1 of the wafers 40. In order to capture the image of the round area 42 of the circumference 1, the wafers 40 need to rotate about its central axis 9 within the cassette 21. Also, in capturing the images of the linear 41 of the circumference 1, either the wafers 40 or the camera 11 is linearly moved with reference to the other. In the scanning of the linear portion 41 of the wafer circumference 1, for example, the camera 11 captures images from the reference point (for example, the right junction between the linear portion 41 and round portion 42 in FIG. 6) to the other (left) junction. During this linear portion scanning, the wafers 40 constantly and linearly moves so that the camera 11 can capture the images from the right junction to the left junction.

When the operator commands the commencement of the wafer inspection using the input unit 90, the system control unit 50 controls the linear movement of the linear motion mechanism 30 of the wafer moving unit 19 accordingly. The step motor 31 is activated and the upper table 39 moves in the X-direction through the operation of the ball screw 32. The flat aligner 20 connected with the upper table 39 and the wafers 40 therein moves in the X-direction at a constant speed. The images of the linear portions 41 of the wafer circumference 1 are captured by the camera 11 as the wafers 40 move linearly. The camera 11 preferably captures continuous images of the circumference 1 as the wafer 40 moves, although not limited thereto. The positions of the upper table 39 and accordingly of the wafers 40 are detected by the sensors 34 installed in the lower table 38. The linear motion of the wafer 40 is continuously controlled by the system control unit 50, and thus the entire area of the linear portion 41 of the circumference is scanned.

Now capturing of images of the round portion 42 of the wafer circumference 1 is discussed. Before the scanning of the round portion 42, the position of the wafers 40 relative to the camera 11 is set. First, the flat aligner 20 containing the wafers 40 is linearly moved to the point where the camera 11 is directly over the central axis 9 of the round portion 42 of the wafers 40. Then, the wafers 40 can be rotated so that the camera 11 can view the starting point of the scan of the round portion 42, for example, the predetermined reference point (the right junction of the linear 41 and the curved portion 42) is positioned right below the central axis (not shown) of the camera lens 12. Then, as the wafers 40 rotate about the central axis 9, the camera 11 captures the images of the round portion 42 of the wafers 40. This wafer rotation is effected by rotation of the roller 23 in contact with the round portion 42 of the wafers 40 according to the instruction from the system control unit 50.

The image information obtained is transmitted to the data storage unit 60 for temporary storage before its processing or directly to the data processing unit 70 for processing. The image process algorithm used by the data processing unit 70 analyzes these data to identify cracks and other defects on the circumference 1 of the wafers 40. An exemplary data processing algorithm compares the image information a flawless wafer 40 with the information of the captured images of the wafers, which are being inspected. Alternatively, the algorithm may identify defects based on data irregularities of a location with reference to the data of other locations on the circumference of the same wafer. Data indicating irregularities may include intensity or angle of the light reflected from the defected surface of the circumference of the wafer. As mentioned above, any algorithms, which can identify defects or flaws from the captured image information, can be used by the data processing unit 70.

Once the inspection for defects on the circumference 1 of the wafer 40 is completed by the data processing unit 70, the data is stored in the data storage unit 60 and displayed in the display unit 80. The displayed data in the display unit 80 or a report summarizing the inspection results can be printed out in a printer. The image of a particular wafer 40 can also be displayed or printed out by identifying the lot number of the wafer.

Figure 9:
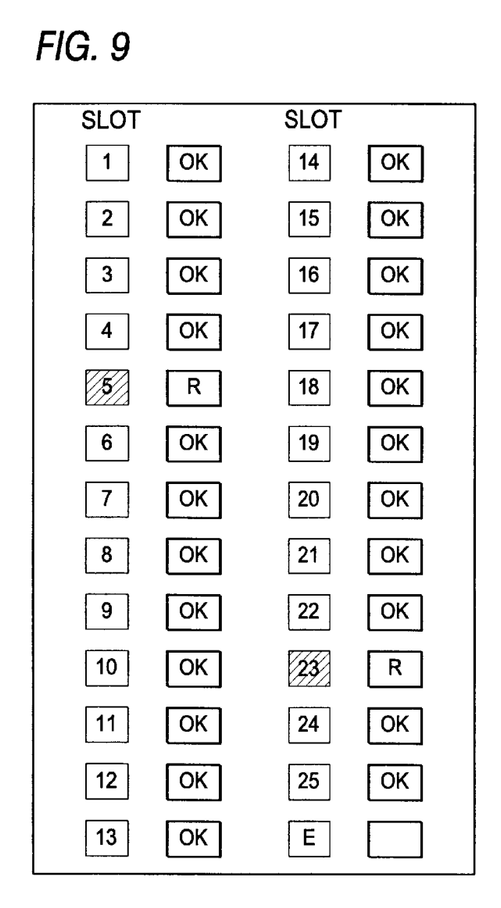
FIG. 9 is an exemplary view displaying wafer circumference inspection results.

FIG. 9 shows a data inspection result display by the display unit 80 in accordance with the embodiment of this invention. The display indicates defects on the circumference of the fifth and twenty third wafers. On the left side of the display, the circumference conditions of 25 wafers are displayed. For instance, the word "OK" appearing beside the serial numbers of wafer slot numbers represents "No significant defects" or "No defects at all". On the other hand, the letter "R" in a different color represents "Existence of significant defects" or "Existence of any defects". If the wafer number of a defective wafer or the letter "R" is clicked, the corresponding lot number and the serial number of the defective wafer is displayed on the upper right portion of the screen, and the locations, sizes, and count of defects are displayed below. The defects of different types or different size ranges may also be displayed with, for example different colors, as shown in FIG. 9.

In the embodiment of this invention discussed above, the linear portion 41 and the curved portion 42 of the circumference 1 of the wafer 40 are scanned with different types of motions of the wafers 40. The linear portion 41 is scanned while linearly moving the wafers 40, yet the round portion 42 is scanned while rotating the wafers 40 about their central axis 9. However, the images of the linear portion 41 can also be captured without having to linearly move the wafers. Instead, the camera 11 can be linearly moved. Alternatively, the same can be done by changing directions of at least one of the camera lens 12 and the light source 15 such that the camera 11 can scan the whole area of the linear portion 41. In this case, the algorithm for processing the data for the linear area may have to be adjusted. Although the embodiments of this invention is discussed in terms of the wafers having both the linear portion 41 and the round portion 42, the present invention can be used to inspect any other types and sizes of the wafers including wafers having a notch. When inspecting the circumference of wafers having a notch, the linear moving mechanism 30 is moved after placing the wafers in the cassette 21 of the flat aligner 20 so that the central axis of the circular wafer is lined up with the central axis of the camera lens 12. Then, the flat aligner 20 is activated to align the pre-selected reference position (for instance, notch). Subsequently, the wafer is rotated and the circumference is scanned to obtain image information.

According to the apparatus and method for inspecting circumference, the wafers with defects on the circumference can be identified before they are subjected to various processes. Therefore, losses of wafers and/or to the semiconductor processing machines due to breakage of wafers, which may be caused by defects on the circumference, can be prevented. Furthermore, the inspection process does not require any changes to the existing equipment for wafer fabrication processes.

Although the invention has been shown and described with respect to the exemplary embodiments, it should be understood that various changes, modifications and additions might be made without departing from the spirit and scope of the invention.

What is claimed is:

1. An apparatus for inspecting defects in a wafer, wherein the wafer is a thin plate comprising two planar surfaces and a circumference forming a thickness of the thin plate, the apparatus comprising:
    a wafer holder;
    a camera configured to capture images of a circumference of a wafer subject to the inspection and to generate data of the captured images; and
    a processor configured to process the data from the camera so as to identify defects on the circumference of the wafer.

2. The apparatus of claim 1, wherein the camera is configured to continuously capture the images of the circumference.

3. The apparatus of claim 1, further comprising a mechanism configured to effect at least one of linear movement of a camera location and changes of a camera direction.

4. The apparatus of claim 1, further comprising a light source configured to illuminate the circumference of the wafer.

5. The apparatus of claim 4, wherein the light source comprises a longitudinal light bulb having a longitudinal direction, and wherein the wafer holder is configured to hold the wafer such that the two surfaces of the wafer is substantially parallel to the longitudinal direction of the light bulb.

6. The apparatus of claim 1, wherein the wafer holder is configured to hold the wafer in a way that the camera captures the images of the circumference of the wafer.

7. The apparatus of claim 6, wherein the holder is configured to hold a plurality of wafers, which are concurrently subject to the inspection.

8. The apparatus of claim 6, further comprising a mechanism configured to couple with the holder, wherein the mechanism is configured to move the wafer held in the wafer holder without changing a distance between the camera and a point on the circumference, which is the closest from the camera.

9. The apparatus of claim 6, further comprising a mechanism configured to keep an angle between a central axis of a lens of the camera directing a point on the circumference and a tangent of the point constant during the capturing images.

10. The apparatus of claim 6, wherein the mechanism is configured to linearly move the holder.

11. The apparatus of claim 9, wherein the mechanism comprises a lower support table and an upper linear motion table configured to linearly move on the lower support table while being coupled therewith.

12. The apparatus of claim 11, wherein the upper linear motion table is configured to couple with the wafer holder.

13. The apparatus of claim 11, wherein the mechanism further comprises an actuator driving the upper linear motion table to linearly move.

14. The apparatus of claim 6, wherein the mechanism is configured to rotate the wafer held in the holder about an axis substantially perpendicular to the surfaces of the wafer.

15. The apparatus of claim 1, wherein the wafer holder comprises a flat aligner, which further comprises a mechanism configured to rotate the wafer held in the holder about an axis substantially perpendicular to the surfaces of the wafer.

16. The apparatus of claim 1, further comprising a display configured to display inspection results.

17. The apparatus of claim 1, further comprising an input device configured to input information relating to the wafer subject to the inspection and commands to the apparatus.

18. The apparatus of claim 1, further comprising a memory configured to store image data of circumference of the wafer.

19. The apparatus of claim 1, wherein the camera comprising a charge coupled device (CCD) line scan camera.

20. A method of inspecting defects on a circumference of a wafer using the apparatus of claim 1, wherein the wafer is a thin plate comprising two surfaces and a circumference neighboring the two surfaces, the method comprising:
   obtaining images of a circumference of a wafer;
   generating data indicative of the images of the circumference; and
   processing the data, thereby identifying defects on the circumference of the semiconductor wafer.

21. The method of claim 20, wherein the obtaining images comprises capturing images of an entire circumference of the wafer with the camera.

22. The method of claim 21, wherein the camera comprising a charge coupled device (CCD) line scan camera.

23. The method of claim 21, wherein the obtaining images further comprises moving at least one of the wafer and the camera.

24. The method of claim 23, wherein the moving is performed without changing a distance between the camera and a point of the circumference, which is the closest from the camera.

25. The method of claim 23, wherein the capturing is performed while the moving is performed.

26. The method of claim 23, wherein the moving comprises linearly moving at least one of the wafer and the camera.

27. The method of claim 26, wherein the wafer circumference comprises a round portion and a linear portion, and wherein during capturing images of the linear portion, the linear moving is performed.

28. The method of claim 23, wherein the moving comprises rotating the wafer about an axis substantially perpendicular to the surfaces of the wafer.

29. The method of claim 28, wherein the wafer surfaces are substantially circular and the axis is a central axis of the circular surfaces.

30. The method of claim 29, wherein in capturing images while rotating the wafer, the camera directs the central axis of the circular surfaces.

31. The method of claim 28, wherein the wafer circumference comprises a round portion and a linear portion, and wherein during capturing images of the round portion, the rotation is performed.

32. The method of claim 20, wherein the obtaining images comprises capturing images of circumference of a plurality of wafers.

33. The method of claim 21, wherein during the capturing images, an angle between a central axis of a lens of the camera directing a point on the circumference and a tangent of the point is kept constant.

34. The method of claim 20, further comprising illuminating the circumference of the wafer during the obtaining of the images.

35. The method of claim 34, wherein the illuminating comprises illuminating the circumference with a longitudinal light source having a longitudinal direction, and wherein the longitudinal direction of the light source is substantially parallel to the surfaces of the wafer.

36. A method of fabricating integrated circuits on a semiconductor wafer, comprising:
   inspecting defects on a circumference of a semiconductor wafer using the apparatus of claim 1;
   thereafter subjecting the semiconductor wafer to at least one of chemical and thermal treatments, thereby fabricating integrated circuits; and
   wherein the inspecting defects comprises:
      capturing images of a circumference of a semiconductor wafer,
      generating data indicative of the images of the circumference, and
      processing the data, thereby identifying defects on the circumference of the semiconductor wafer.

* * * * *